United States Patent
Iizuka et al.

(10) Patent No.: US 11,325,072 B2
(45) Date of Patent: May 10, 2022

(54) OBJECT TRAPPING DEVICE AND OBJECT TRAPPING DEVICE UNIT

(71) Applicants: SHARP KABUSHIKI KAISHA, Sakai (JP); The University of Tokyo, Tokyo (JP)

(72) Inventors: Kunihiko Iizuka, Sakai (JP); Takeshi Mitsunaka, Sakai (JP); Yoshihisa Fujimoto, Sakai (JP); Teruo Fujii, Tokyo (JP); Soo-Hyeon Kim, Tokyo (JP)

(73) Assignees: SHARP KABUSHIKI KAISHA, Sakai (JP); The University of Tokyo, Tokyo (JP)

( * ) Notice: Subject to any disclaimer, the term of this patent is extended or adjusted under 35 U.S.C. 154(b) by 182 days.

(21) Appl. No.: 16/500,089

(22) PCT Filed: Mar. 23, 2018

(86) PCT No.: PCT/JP2018/011807
§ 371 (c)(1),
(2) Date: Oct. 1, 2019

(87) PCT Pub. No.: WO2018/198621
PCT Pub. Date: Nov. 1, 2018

(65) Prior Publication Data
US 2021/0101115 A1  Apr. 8, 2021

(30) Foreign Application Priority Data
Apr. 24, 2017 (JP) .............................. JP2017-085579

(51) Int. Cl.
*B03C 5/02* (2006.01)
*B03C 5/00* (2006.01)
(Continued)

(52) U.S. Cl.
CPC .............. *B01D 57/02* (2013.01); *B03C 5/005* (2013.01); *B03C 5/026* (2013.01); *C12M 47/04* (2013.01);
(Continued)

(58) Field of Classification Search
CPC .. B03C 5/005; B03C 5/026; G01N 27/44773; G01N 27/33791
See application file for complete search history.

(56) References Cited

U.S. PATENT DOCUMENTS

2007/0243634 A1* 10/2007 Pamula ............ B01L 3/502715
                                                    436/518
2008/0252566 A1   10/2008 Kawase et al.

FOREIGN PATENT DOCUMENTS

EP     2428560 A1 *  3/2012  ............. B03C 5/026
JP     2008-224839 A   9/2008
(Continued)

OTHER PUBLICATIONS

S. H. Kim, Efficient analysis of a small number of cancer cells at the single-cell level using an electroactive double-wall array, Lab Chip, 2016 (16), p. 2440-49. (Year: 2016).*
(Continued)

*Primary Examiner* — Luan V Van
*Assistant Examiner* — Caitlyn Mingyun Sun
(74) *Attorney, Agent, or Firm* — ScienBiziP, P.C.

(57) ABSTRACT

An object trapping device enables efficiently trapping a plurality of objects in a specific combination. Each of a first electrode pair (13), a second electrode pair (14), and a third electrode pair (15) in an electrode pair group (3) is applied with an individual AC voltage and traps an object by dielectrophoresis generated in accordance with the AC voltage that is applied.

5 Claims, 12 Drawing Sheets

(51) Int. Cl.
*B01D 57/02* (2006.01)
*C12M 1/00* (2006.01)
*G01N 27/447* (2006.01)

(52) U.S. Cl.
CPC . *G01N 27/44773* (2013.01); *G01N 27/44791* (2013.01)

(56) References Cited

FOREIGN PATENT DOCUMENTS

WO 2016/040476 A1 3/2016
WO WO-2020231399 A1 * 11/2020 ....... G01N 33/54386

OTHER PUBLICATIONS

ChunHui Wu et al.: "A planar dielectrophoresis-based chip for high-throughput cell pairing", Lab on a Chip, Dec. 7, 2017, vol. 17, p. 4008-4014, Abstract, fig. 1-4.
Alison M Skelley, Oktay Kirak, Heikyung Suh, Rudolf Jaenisch, & Joel Voldman: "Microfluidic control of cell pairing and fusion", Nature Methods, vol. 6, No. 2, pp. 147-152, Feb. 2009.
Macosko E. Z. et al.: "Highly Parallel Genome-wide Expression Profiling of Individual Cells Using Nanoliter Droplets", Cell 161, 1202-1214, May 21, 2015.

* cited by examiner

| | |
|---|---|
| 1: OBJECT TRAPPING DEVICE | 13: FIRST ELECTRODE PAIR |
| 2: SEMICONDUCTOR SUBSTRATE | 14: SECOND ELECTRODE PAIR |
| 3: ELECTRODE PAIR GROUP | 15: THIRD ELECTRODE PAIR |
| 11: WELL FORMATION LAYER | 16: WELL |
| 12: CONTROL CIRCUIT | 17: PROTECTION FILM |

1a: OBJECT TRAPPING DEVICE
2: SEMICONDUCTOR SUBSTRATE
3: ELECTRODE PAIR GROUP
11: WELL FORMATION LAYER
12a: CONTROL CIRCUIT
13: FIRST ELECTRODE PAIR
14: SECOND ELECTRODE PAIR
15: THIRD ELECTRODE PAIR
16: WELL
17: PROTECTION FILM
18: PHOTODIODE

| 1b: OBJECT TRAPPING DEVICE | 15: THIRD ELECTRODE PAIR |
| 2: SEMICONDUCTOR SUBSTRATE | 16: WELL |
| 3: ELECTRODE PAIR GROUP | 17: PROTECTION FILM |
| 11: WELL FORMATION LAYER | 19: SUB-WELL FORMATION LAYER |
| 12: CONTROL CIRCUIT | 23: FIRST SUB-WELL |
| 13: FIRST ELECTRODE PAIR | 24: SECOND SUB-WELL |
| 14: SECOND ELECTRODE PAIR | 25: THIRD SUB-WELL |

FIG. 10

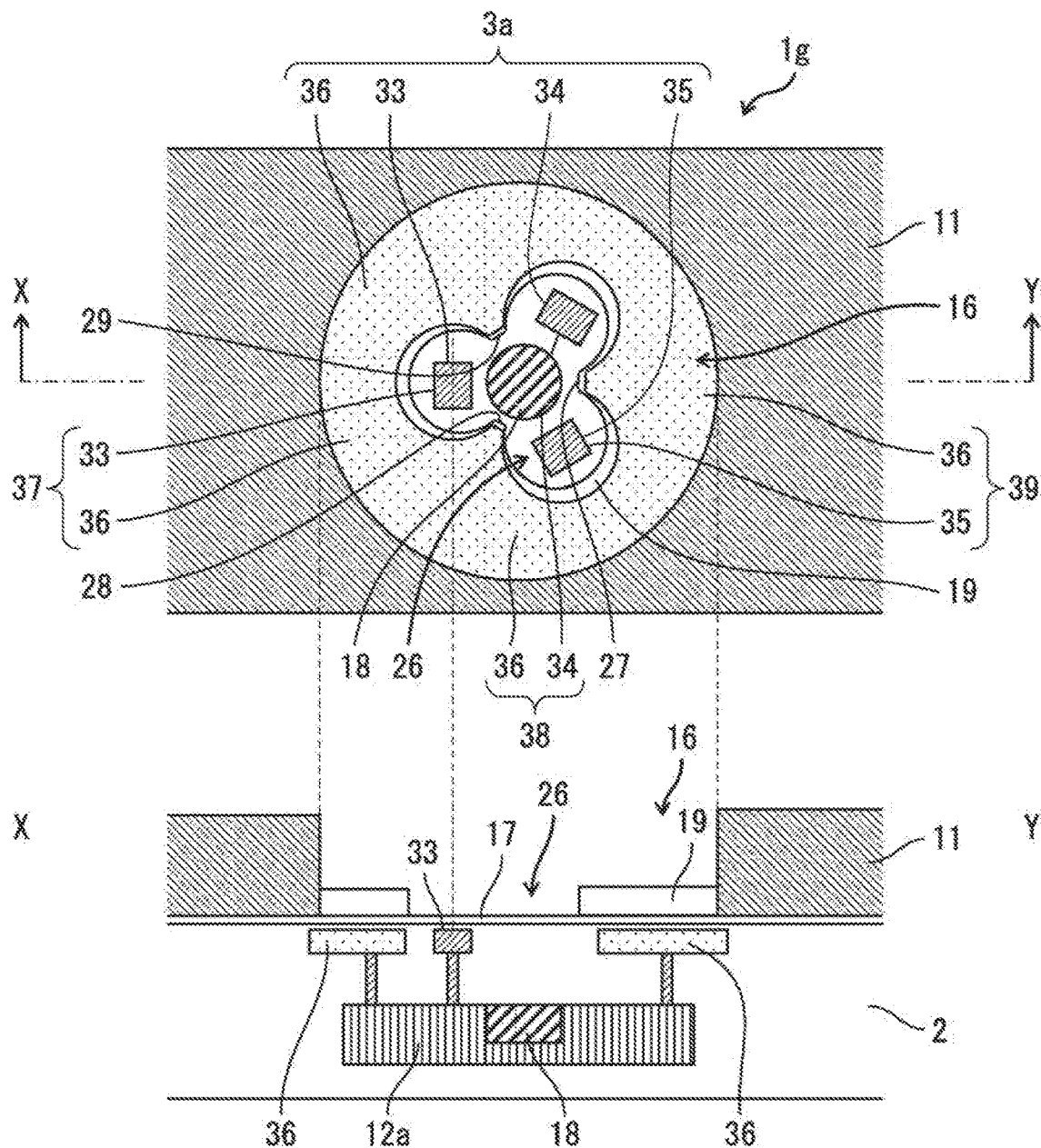

| | |
|---|---|
| 1g: OBJECT TRAPPING DEVICE | 27: NARROWED PORTION |
| 2: SEMICONDUCTOR SUBSTRATE | 28: NARROWED PORTION |
| 3a: ELECTRODE PAIR GROUP | 29: NARROWED PORTION |
| 11: WELL FORMATION LAYER | 33: FRIST ELECTRODE |
| 12a: CONTROL CIRCUIT | 34: SECOND ELECTRODE |
| 16: WELL | 35: THIRD ELECTRODE |
| 17: PROTECTION FILM | 36: COMMON ELECTRODE |
| 18: PHOTODIODE | 37: FIRST ELECTRODE PAIR |
| 19: SUB-WELL FORMATION LAYER | 38: SECOND ELECTRODE PAIR |
| 26: SUB-WELL SET | 39: THIRD ELECTRODE PAIR |

OBJECT TRAPPING DEVICE AND OBJECT TRAPPING DEVICE UNIT

TECHNICAL FIELD

The present invention relates to an object trapping device and an object trapping device unit.

BACKGROUND ART

In analysis of molecules or cells, a specific combination of target cells or minute biological or non-biological sample materials needs to be introduced into a microwell, for example, in a case of evaluating an interaction between specific cells or a case of evaluating reactions of an object to various reagents.

For example, as described in NPL 1, in order to analyze a gene expression pattern of cells, it is effective to apply a barcode according to a DNA sequence that is different between individual cells to mRNA derived from each of the individual cells. As a method of achieving such application of the barcode, it is necessary to introduce one microbead and one cell into a microwell.

An existing method of using a microwell in which objects are diffused in a fluid and a probabilistically expected combination of objects is trapped, an existing method of causing cells and microbeads to flow in a fluidic path and using droplets which are formed in oil and in which a probabilistically expected combination of objects is trapped, and the like have been adopted. The former is disclosed in NPL 2 and the latter is disclosed in PTL1 and NPL 1, respectively.

Specifically, as a method of evaluating an interaction between specific cells, NPL 2 discloses a method of trapping two kinds of cells.

A fluidic device disclosed in NPL 2 is a fluidic device 110 in which a plurality of H-shaped trap grooves 111 illustrated in FIG. 11(a) and formed by silicone rubber represented by PDMS (polydimethylsiloxane), resin, or the like are arrayed as illustrated in FIG. 11(b). Each of the H-shaped trap grooves 111 has a first cavity 112 at one side and a second cavity 113 at the other side. The second cavity 113 is structured so as to have a cavity slightly smaller than the first cavity 112. The fluidic device 110 has a structure with a mechanism in which a liquid culture medium containing cells and liquid such as a buffer solution flow from a Z direction to a W direction and from the W direction to the Z direction.

FIGS. 12(a) to 12(c) briefly illustrate a procedure until two kinds of cells A and B are trapped and an interaction between the cells is caused. As illustrated in FIG. 12(a), liquid containing cells A of a first type is put in the fluidic device 110 and caused to flow from the W direction to the Z direction. A cell A is sequentially inserted (trapped) in the second cavity 113 of the H-shaped trap groove 111. At this time, since the second cavity 113 is small, a plurality of cells A are not trapped in the same H-shaped trap groove 111.

Next, as illustrated in FIG. 12(b), the liquid containing the cells A is caused to flow in a reverse direction (from the Z direction to the W direction). A cell A is trapped in the first cavity 112 downstream the second cavity 113. Since the H-shaped trap grooves 111 are arranged in zigzag and first cavities 112 exist downstream second cavities 113, a plurality of cells A are able to be moved to the first cavities 112 at once as long as a flow rate is appropriately adjusted.

Immediately after the cells A are moved to the respective first cavities 112, liquid containing cells B of a second type is caused to flow from the Z direction to the W direction as illustrated in FIG. 12(c). By appropriately adjusting each of the first cavities 112 to have such a size that allows one cell A and one cell B to be put therein, one cell B is trapped in the first cavity 112 in which the cell A is trapped. Then, for causing an interaction between the cells, adjacent different cells (here, the cell A and the cell B) are subjected to a treatment of an osmotic shock method or the like.

CITATION LIST

Patent Literature

PTL 1: WO2016/040476 (published on Mar. 17, 2016)

Non Patent Literature

NPL 1: Macosko E. Z. et al., "Highly Parallel Genome-wide Expression Profiling of Individual Cells Using Nanoliter Droplets" Cell 161, 1202-1214, May 21, 2015

NPL 2: Alison M Skelley, Oktay Kirak, Heikyung Suh, Rudolf Jaenisch, & Joel Voldman, "Microfluidic control of cell pairing and fusion", NATURE METHODS, VOL. 6, NO. 2, pp. 147-152, FEBRUARY 2009

SUMMARY OF INVENTION

Technical Problem

In the method disclosed in PTL 1 and NPL 1, the number of droplets in each of which one cell and one microbead are introduced is only several thousands while several millions of droplets are generated in an hour. Thus, there is a problem that many samples are wasted and processing takes time.

Moreover, a fluidic device disclosed in NPL 2 has a configuration in which two kinds of cells are trapped in many sites. The fluidic device has problems that it is difficult to change a combination of cells for each of the sites, it is difficult to seal the site, and it is difficult to create a combination of three or more cells.

Note that, due to difficulty in sealing the site, the following disadvantage is caused. That is, the method of NPL 2 has difficulty in sealing a site, in which cells are trapped, for separation from another site. Thus, it is difficult to prevent a reaction product caused in one site from being diffused to another site, and therefore, whether to be an individual reaction in each site is difficult to be checked. This means that an experiment premising that an individual phenomenon occurs in each site is difficult to be conducted, and an application range of a technique is limited.

Accordingly, each of the techniques of the related art described above poses a problem that it is inefficient to trap a plurality of objects in a specific combination.

An aspect of the invention aims to achieve an object trapping device and an object trapping device unit that are able to efficiently trap a plurality of objects in a specific combination.

Solution to Problem

In order to solve the aforementioned problems, an object trapping device according to an aspect of the invention includes a well, and an electrode pair group that is arranged in a bottom part of the well and includes a plurality of electrode pairs, in which each of the plurality of electrode pairs in the electrode pair group is applied with an individual AC voltage and traps an object by dielectrophoresis generated in accordance with the AC voltage that is applied, and each of sub-wells is arranged above a corresponding one of the plurality of electrode pairs.

In order to solve the aforementioned problems, an object trapping device unit according to an aspect of the invention includes a first object trapping device that is the object trapping device according to the aspect of the invention, and a second object trapping device that is the object trapping device according to the aspect of the invention and is different from the first object trapping device, in which the second object trapping device traps a substance, which is not trapped by the first object trapping device, as the object.

Advantageous Effects of Invention

According to the aspect of the invention, it is possible to efficiently trap a plurality of objects in a specific combination.

BRIEF DESCRIPTION OF DRAWINGS

FIG. 10 is a plan view and a sectional view taken along a line X-Y each illustrating a configuration of a third modified example of the object trapping device according to Embodiment 3 of the invention.

FIG. 11 is a plan view for explaining a fluidic device disclosed in NPL 2, in which FIG. 11(a) illustrates a configuration of one H-shaped trap groove and FIG. 11(b) illustrates a configuration of the fluidic device constituted by a plurality of H-shaped trap grooves.

FIG. 12 is a plan view briefly illustrating a procedure until two kinds of cells are trapped and an interaction between the cells is caused by the fluidic device disclosed in NPL 2, in which FIG. 12(a) illustrates a step in which liquid containing cells of a first type is put in the fluidic device and caused to flow from a W direction to a Z direction, FIG. 12(b) illustrates a step in which the liquid containing the cells of the first type is caused to flow in a reverse direction (from the Z direction to the W direction), and FIG. 12(c) illustrates a step in which liquid containing cells of a second type is caused to flow from the Z direction to the W direction.

DESCRIPTION OF EMBODIMENTS

Embodiments of the invention will be described with reference to FIGS. 1 to 10. Note that, for simplification of the description, members having the same functions as those of members described before will be given the same reference signs and description thereof will be omitted.

Embodiment 1

Figure 1:
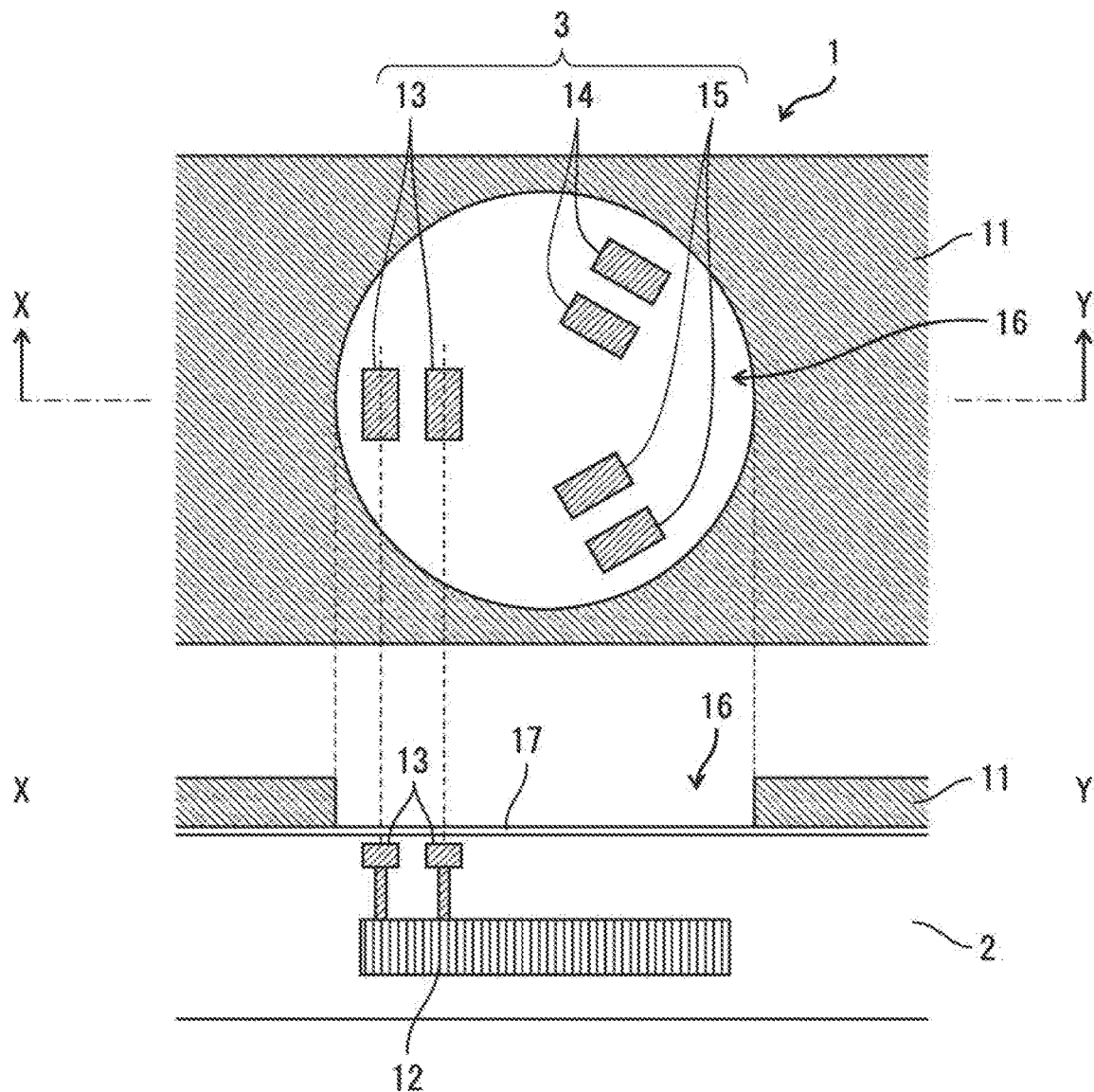
FIG. 1 is a plan view and a sectional view taken along a line X-Y each illustrating a configuration of an object trapping device according to Embodiment 1 of the invention.

FIG. 1 is a plan view and a sectional view taken along a line X-Y each illustrating a configuration of an object trapping device 1 according to Embodiment 1 of the invention. The object trapping device 1 includes a semiconductor substrate 2, an electrode pair group 3, a well formation layer 11, a control circuit 12, and a protection film 17. The electrode pair group 3 has a first electrode pair 13, a second electrode pair 14, and a third electrode pair 15. A well 16 is also formed in the object trapping device 1.

The semiconductor substrate 2 is a substrate constituted by a semiconductor. The protection film 17 is an insulating film that is laminated on the semiconductor substrate 2 and has a function of protecting the semiconductor substrate 2. The well formation layer 11 is laminated on the protection film 17 and constituted by, for example, resin. An opening through which the protection film 17 is exposed is formed in the well formation layer 11 and the opening corresponds to the well 16.

The control circuit 12 is formed in the semiconductor substrate 2. The first electrode pair 13, the second electrode pair 14, and the third electrode pair 15 are arranged in a bottom part of the well 16 in the semiconductor substrate 2 and connected to the control circuit 12. Each of the first electrode pair 13, the second electrode pair 14, and the third electrode pair 15 has a configuration in which two electrodes are paired. Although the first electrode pair 13, the second electrode pair 14, and the third electrode pair 15 are arranged substantially concentrically with an inner wall of the well 16, the arrangement is merely an example.

In the object trapping device 1 including the protection film 17, the electrode pair group 3 and a bottom surface of the well 16 are not conductive, and therefore, when liquid is put in the well 16, the electrode pair group 3 and the liquid are prevented from being conductive. In a case where it is not necessary to prevent the electrode pair group 3 and the liquid from being conductive, the protection film 17 may be omitted.

Figure 2:
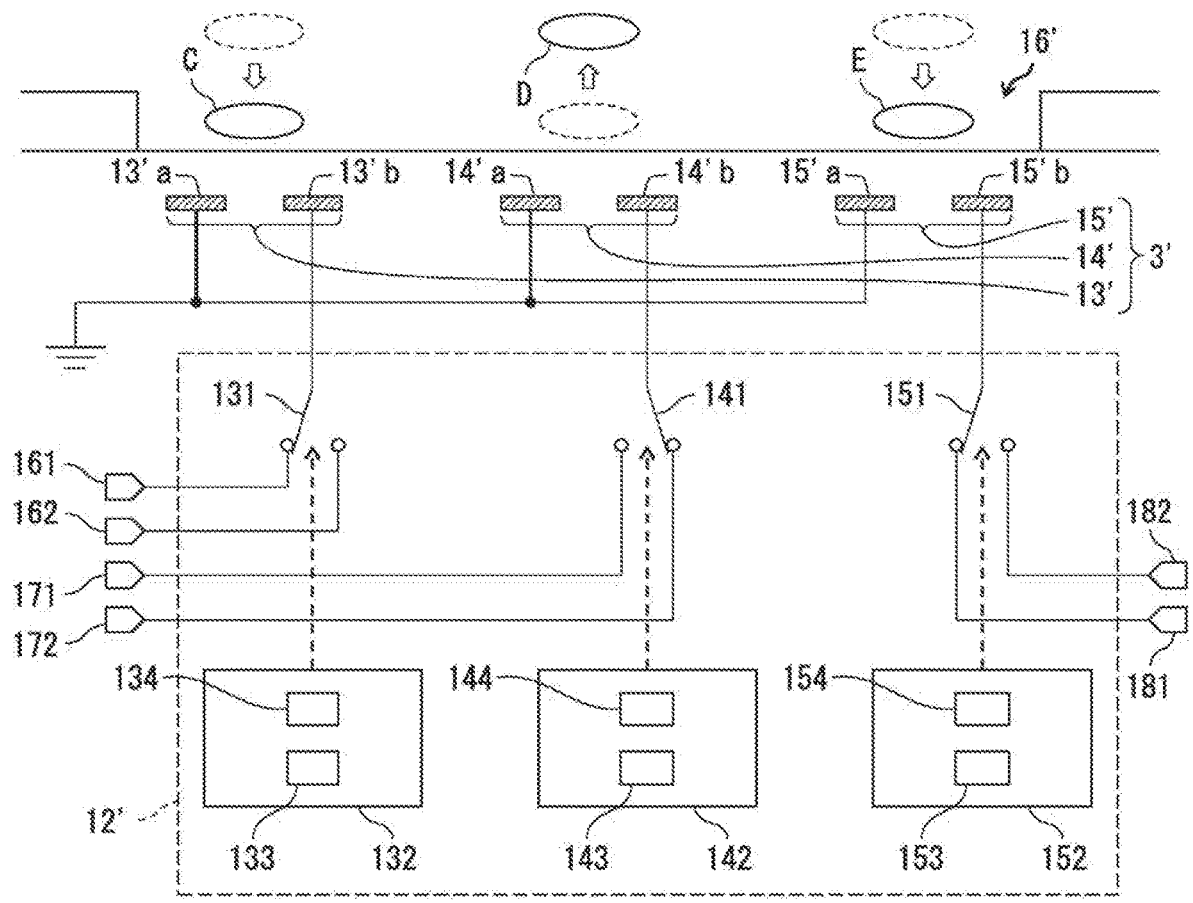
FIG. 2 illustrates an image of trapping an object by an electrode pair group.

FIG. 2 illustrates an image of trapping an object by an electrode pair group 3'. The electrode pair group 3' traps an object by a principle of dielectrophoresis. The electrode pair group 3' has a first electrode pair 13', a second electrode pair 14', and a third electrode pair 15'. The first electrode pair 13', the second electrode pair 14', and the third electrode pair 15' are connected to a control circuit 12'. The electrode pair group 3', the control circuit 12', the first electrode pair 13', the second electrode pair 14', and the third electrode pair 15' respectively correspond to the electrode pair group 3, the control circuit 12, the first electrode pair 13, the second electrode pair 14, and the third electrode pair 15 which are illustrated in FIG. 1. Further, a well 16' in FIG. 2 corresponds to the well 16 illustrated in FIG. 1.

The control circuit 12' has a switch 131, a switch setting unit 132, a switch 141, a switch setting unit 142, a switch 151, and a switch setting unit 152. One electrode 13'*a* of the first electrode pair 13', one electrode 14'*a* of the second electrode pair 14', and one electrode 15'*a* of the third electrode pair 15' are all grounded. The other electrode 13'*b* of the first electrode pair 13', the other electrode 14'*b* of the second electrode pair 14', and the other electrode 15'*b* of the third electrode pair 15' are respectively connected to one end of the switch 131, one end of the switch 141, and one end of the switch 151.

The other end of the switch 131 is switched between a state of being connected to a voltage source 161 that generates an AC voltage to attract a cell (object) C and a state of being connected to a voltage source 162 that generates an AC voltage to keep the cell C at a distance. Whether the other end of the switch 131 is to be connected to the voltage source 161 or to the voltage source 162 is set by the switch setting unit 132. The switch setting unit 132 is constituted by a memory 133 in which a condition under which the other end of the switch 131 is connected to the voltage source 161 and a condition under which the other end of the switch 131 is connected to the voltage source 162 are stored, and a control unit 134 that reads the conditions stored in the memory 133 and controls the switch 131 in accordance with the read conditions. The control unit 134 is constituted by, for example, a CPU (central processing unit) or a well-known switch control circuit.

The other end of the switch 141 is switched between a state of being connected to a voltage source 171 that generates an AC voltage to attract a cell (object) D and a state of being connected to a voltage source 172 that generates an AC voltage to keep the cell D at a distance. Whether the other end of the switch 141 is to be connected to the voltage source 171 or to the voltage source 172 is set by the switch setting unit 142. The switch setting unit 142 is constituted by a memory 143 in which a condition under which the other end of the switch 141 is connected to the voltage source 171 and a condition under which the other end of the switch 141 is connected to the voltage source 172 are stored, and a control unit 144 that reads the conditions stored in the memory 143 and controls the switch 141 in accordance with the read conditions. The control unit 144 is constituted by, for example, a CPU or a well-known switch control circuit.

The other end of the switch 151 is switched between a state of being connected to a voltage source 181 that generates an AC voltage to attract a cell (object) E and a state of being connected to a voltage source 182 that generates an AC voltage to keep the cell E at a distance. Whether the other end of the switch 151 is to be connected to the voltage source 181 or to the voltage source 182 is set by the switch setting unit 152. The switch setting unit 152 is constituted by a memory 153 in which a condition under which the other end of the switch 151 is connected to the voltage source 181 and a condition under which the other end of the switch 151 is connected to the voltage source 182 are stored, and a control unit 154 that reads the conditions stored in the memory 153 and controls the switch 151 in accordance with the read conditions. The control unit 154 is constituted by, for example, a CPU or a well-known switch control circuit.

The first electrode pair 13' generates an electric field in accordance with the AC voltage applied from any one of the voltage source 161 and the voltage source 162 to the electrode 13'*b*. When an angular frequency of the AC voltage is ω, a dielectrophoretic force is applied by the electric field to a dielectric particle contained in liquid near the first electrode pair 13'. The dielectrophoretic force is represented by the following mathematical formula with use of a complex dielectric constant of the liquid $\varepsilon_m^* = \varepsilon_m - j\sigma_m/\omega$, a complex dielectric constant of the dielectric particle $\varepsilon_p^* = \varepsilon_p - j\sigma_p/\omega$, a radius r of the dielectric particle, and an effective value of intensity of the generated electric field.

$$\langle \vec{F}_{DEP} \rangle = \pi \varepsilon_m r^3 \mathrm{Re}\left[\frac{\varepsilon_p^* - \varepsilon_m^*}{\varepsilon_p^* + 2\varepsilon_m^*}\right] \nabla |\vec{E}_{RMS}|^2 \qquad \text{[Mathematical formula 1]}$$

Here, $\langle \vec{F}_{DEP} \rangle$ indicates the dielectrophoretic force acting on the dielectric particle in the liquid and $|\vec{E}_{RMS}|$ indicates an effective value of intensity of an electric field generated by a sine-wave voltage.

When $\mathrm{Re}[(\varepsilon_p^* - \varepsilon_m^*)/(\varepsilon_p^* + 2\varepsilon_m^*)]$ in the mathematical formula is positive, a force toward a direction in which the intensity of the generated electric field is high, that is, a positive dielectrophoretic force acts on the dielectric particle. On the other hand, when $\mathrm{Re}[(\varepsilon_p^* - \varepsilon_m^*)/(\varepsilon_p^* + 2\varepsilon_m^*)]$ in the mathematical formula is negative, a force against the force toward the direction in which the intensity of the generated electric field is high, that is, a negative dielectrophoretic force acts on the dielectric particle.

A position where the intensity of the electric field generated near the first electrode pair 13' is highest is intermediate between the electrode 13'*a* and the electrode 13'*b* that are paired with each other. Thus, when such an AC voltage of an angular frequency $\omega_p$ that generates the positive dielectrophoretic force is applied to the electrode 13'*b*, the dielectric particle in the liquid is attracted to a part intermediate between the electrode 13'*a* and the electrode 13'*b*, and therefore, the dielectric particle is able to be trapped. In other words, when an angular frequency of the AC voltage output by the voltage source 161 is the angular frequency $\omega_p$, the dielectric particle is able to be trapped while the electrode 13'*b* is connected to the voltage source 161.

On the other hand, when such an AC voltage of an angular frequency $\omega_n$ that generates the negative dielectrophoretic force is applied to the electrode 13'*b*, the dielectric particle in the liquid is kept at a distance from the part intermediate between the electrode 13'*a* and the electrode 13'*b*, and therefore, the dielectric particle is able to be released. In other words, when an angular frequency of the AC voltage output by the voltage source 162 is the angular frequency on, the dielectric particle is able to be released while the electrode 13'*b* is connected to the voltage source 162.

Note that, an example of the AC voltage output by the voltage source 161 includes a voltage with an amplitude of 2 V and a frequency of 5 MHz. However, an optimum amplitude and an optimum frequency of the AC voltage output by the voltage source 161 vary depending on, for example, a size of the dielectric particle in addition to the complex dielectric constant of the liquid, the complex dielectric constant of the dielectric particle, and the radius of the dielectric particle.

The AC voltage output by the voltage source 161 is set so that the first electrode pair 13' traps the cell C, and the AC voltage output by the voltage source 162 is set so that the first electrode pair 13' releases the cell C. Accordingly, the first electrode pair 13' is able to trap and release the cell C as the dielectric particle (the foregoing is the principle of dielectrophoresis).

By a principle similar to that of the first electrode pair 13', the second electrode pair 14' and the third electrode pair 15' are also able to trap and release a dielectric particle. That is, the AC voltage output by the voltage source 171 is set so that the second electrode pair 14' traps the cell D, and the AC voltage output by the voltage source 172 is set so that the second electrode pair 14' releases the cell D. Accordingly, the second electrode pair 14' is able to trap and release the cell D as the dielectric particle. Further, the AC voltage output by the voltage source 181 is set so that the third electrode pair 15' traps the cell E, and the AC voltage output by the voltage source 182 is set so that the third electrode pair 15' releases the cell E. Accordingly, the third electrode pair 15' is able to trap and release the cell E as the dielectric particle.

Meanwhile, it is important to trap a plurality of objects in one well 16 to evaluate an interaction between specific cells (objects) or reactions of an object to various reagents. Here, a procedure of trapping a specific combination of objects by the object trapping device 1 will be described.

It is assumed that the first electrode pair 13, the second electrode pair 14, and the third electrode pair 15 respectively trap a cell F, a cell G, and a cell H as objects and the object trapping device 1 traps the cell F, the cell G, and the cell H in this order.

First, liquid containing only the cell F is caused to flow in the object trapping device 1. At this time, the control circuit 12 applies, only to the first electrode pair 13, an AC voltage with an optimum condition under which the cell F is trapped by the principle of dielectrophoresis described above. On the other hand, at this time, to the second electrode pair 14 and the third electrode pair 15, the control circuit 12 does not apply the AC voltage or applies an AC voltage with an optimum condition under which the cell F is released by the principle of dielectrophoresis described above. Accordingly, only the first electrode pair 13 traps the cell F.

Next, liquid containing only the cell G is caused to flow in the object trapping device 1. At this time, the control circuit 12 continuously applies, to the first electrode pair 13, the AC voltage with the optimum condition under which the cell F is trapped by the principle of dielectrophoresis described above. Further, at this time, the control circuit 12 applies, only to the second electrode pair 14, an AC voltage with an optimum condition under which the cell G is trapped by the principle of dielectrophoresis described above. On the other hand, at this time, to the third electrode pair 15, the control circuit 12 does not apply any of the AC voltages or applies an AC voltage with an optimum condition under which the cell F and/or the cell G are/is released by the principle of dielectrophoresis described above. Note that, at this time, since the cell F is continuously trapped by the first electrode pair 13, the cell G is not trapped by the first electrode pair 13. Further, at this time, neither the cell F nor the cell G is trapped by the third electrode pair 15.

Next, liquid containing only the cell H is caused to flow in the object trapping device 1. At this time, the control circuit 12 continuously applies, to the first electrode pair 13, the AC voltage with the optimum condition under which the cell F is trapped by the principle of dielectrophoresis described above and continuously applies, to the second electrode pair 14, the AC voltage with the optimum condition under which the cell G is trapped by the principle of dielectrophoresis described above. Further, at this time, the control circuit 12 applies, to the third electrode pair 15, an AC voltage with an optimum condition under which the cell H is trapped by the principle of dielectrophoresis described above. Note that, at this time, since the cell F and the cell G are continuously trapped by the first electrode pair 13 and the second electrode pair 14, respectively, the cell H is not trapped by the first electrode pair 13 or the second electrode pair 14.

Figure 3:
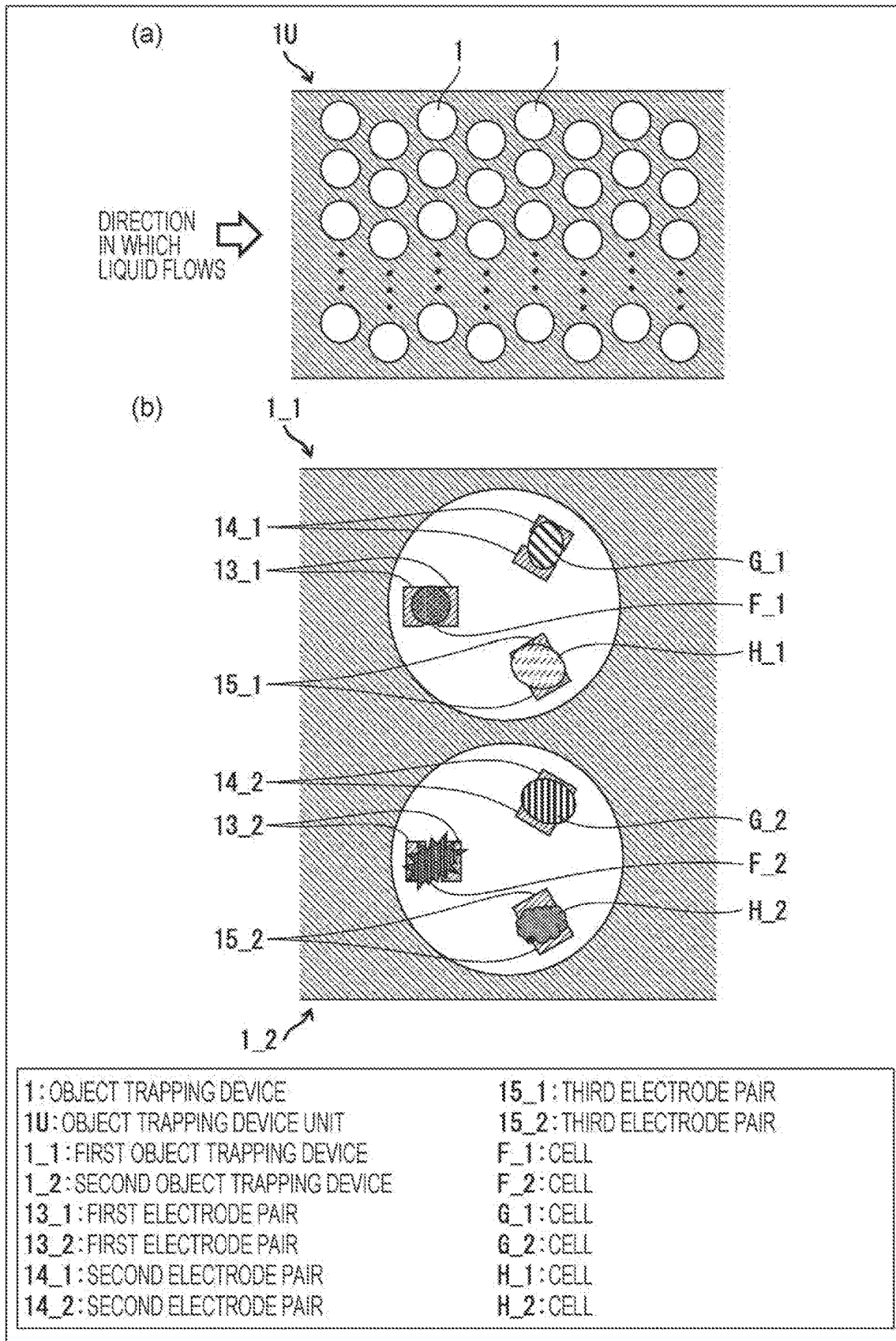
FIG. 3(a) is a plan view schematically illustrating a configuration of an object trapping device unit according to Embodiment 1 of the invention and FIG. 3(b) is an enlarged view of two of a plurality of object trapping devices illustrated in FIG. 3(a).

FIG. 3(*a*) is a plan view schematically illustrating a configuration of an object trapping device unit 1U according to Embodiment 1 of the invention. FIG. 3(*b*) is an enlarged view of two of a plurality of object trapping devices 1 illustrated in FIG. 3(*a*).

The object trapping device unit 1U has the plurality of object trapping devices 1 arranged in zigzag. The plurality of object trapping devices 1 are controlled independently from each other by control circuits 12 (refer to FIG. 1) that are individually provided therein. Thus, when focusing on a first object trapping device 1_1 and a second object trapping device 12 which are two of the plurality of object trapping devices 1, the second object trapping device 1_2 is easily configured to trap a substance, which is not trapped by the first object trapping device 1_1, as an object. This makes it possible to achieve different combinations of objects for the respective object trapping devices 1. An example of such a configuration is illustrated in FIG. 3(*b*).

That is, in FIG. 3(*b*), in the first object trapping device 1_1, a first electrode pair 13_1 corresponding to the first electrode pair 13, a second electrode pair 14_1 corresponding to the second electrode pair 14, and a third electrode pair 15_1 corresponding to the third electrode pair 15 respectively trap a cell F_1, a cell G_1, and a cell H_1. On the other hand, in FIG. 3(*b*), in the second object trapping device 1_2, a first electrode pair 132 corresponding to the first electrode pair 13, a second electrode pair 14_2 corresponding to the second electrode pair 14, and a third electrode pair 15_2 corresponding to the third electrode pair 15 respectively trap a cell F_2, a cell G_2, and a cell H_2.

Of course, the plurality of object trapping devices 1 of the object trapping device unit 1U may be collectively controlled as needed.

Moreover, when an object trapping device 1 has the well 16 on which a lid is put, the object trapping device 1 is able to be used as a minute reaction vessel separated from another object trapping device 1. When an object trapped by the object trapping device 1 is a cell, in order to analyze an inside gene by disrupting a membrane of the cell, at least any one of the first electrode pair 13, the second electrode pair 14, and the third electrode pair 15 may be allowed to generate an electric field that is high enough to disrupt the membrane of the cell. In other words, the control circuit 12 may have a circuit that causes at least one of the first electrode pair 13, the second electrode pair 14, and the third electrode pair 15 to generate an electric field that is high enough to disrupt the membrane of the cell. Moreover, when the control circuit 12 is not able to withstand the high electric field, a cell disrupting electrode that generates the electric field to disrupt the membrane of the cell (and further, a control circuit of the cell disrupting electrode, as needed) may be provided separately.

According to the object trapping device 1, a plurality of electrode pairs attract and trap respective target objects by the principle of dielectrophoresis. Thus, according to the object trapping device 1, it is possible to achieve trapping of a plurality of objects in a specific combination with high probability.

Moreover, as indicated in the object trapping device unit 1U, according to the object trapping devices 1, a combination of objects is able to be differentiated for each of the object trapping devices 1. Further, according to the object trapping device 1, it is possible to easily seal the well 16 by putting a lid on the well 16. Furthermore, according to the object trapping device 1, the electrode pair group 3 including the first electrode pair 13, the second electrode pair 14, and the third electrode pair 15 enables creation of three or more combinations of objects.

Thus, according to the object trapping device 1, it is possible to efficiently trap a plurality of objects in a specific combination.

Moreover, according to the object trapping device unit 1U, it is possible to achieve different combinations of objects for the respective object trapping devices 1. Note that, in the object trapping device unit 1U, any of object trapping devices 1a to 1g described below may be used instead of the object trapping device 1.

Figure 4:
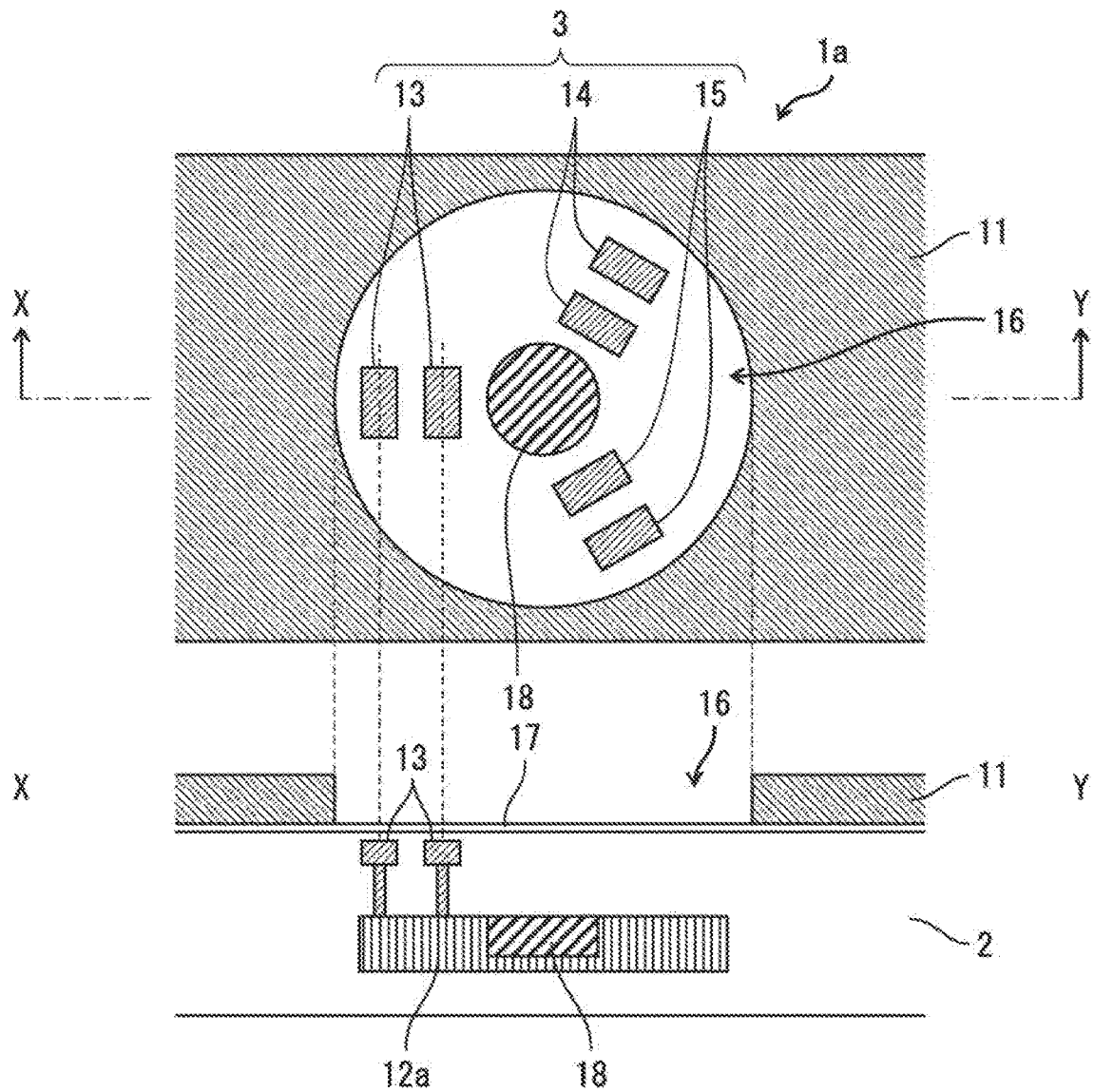
FIG. 4 is a plan view and a sectional view taken along a line X-Y each illustrating a configuration of a modified example of the object trapping device according to Embodiment 1 of the invention.

FIG. 4 is a plan view and a sectional view taken along a line X-Y each illustrating a configuration of the object trapping device 1a which is a modified example of the object trapping device 1 according to Embodiment 1 of the invention. The object trapping device 1a includes a photodiode 18 in addition to the configuration of the object trapping device 1. The photodiode 18 is arranged below the electrode pair group 3 and provided in the control circuit 12 here. Moreover, in plan view of the object trapping device 1a, the photodiode 18 is arranged at a position surrounded by the first electrode pair 13, the second electrode pair 14, and the third electrode pair 15. Here, one in which the photodiode 18 is provided in the control circuit 12 is used as a control circuit 12a.

The object trapping device 1a is suitable for an experiment to evaluate an interaction between a plurality of cells by generation of a fluorescent material. That is, excitation light is radiated by a laser diode (not illustrated) or the like to the well 16 from above the well 16, the fluorescent material is excited by the excitation light, and light caused by the excitation is received by the photodiode 18. Then, by using the light received by the photodiode 18 for evaluation of an interaction between a plurality of cells, the evaluation is able to be conducted without using a fluorescence microscope.

Embodiment 2

Figure 5:
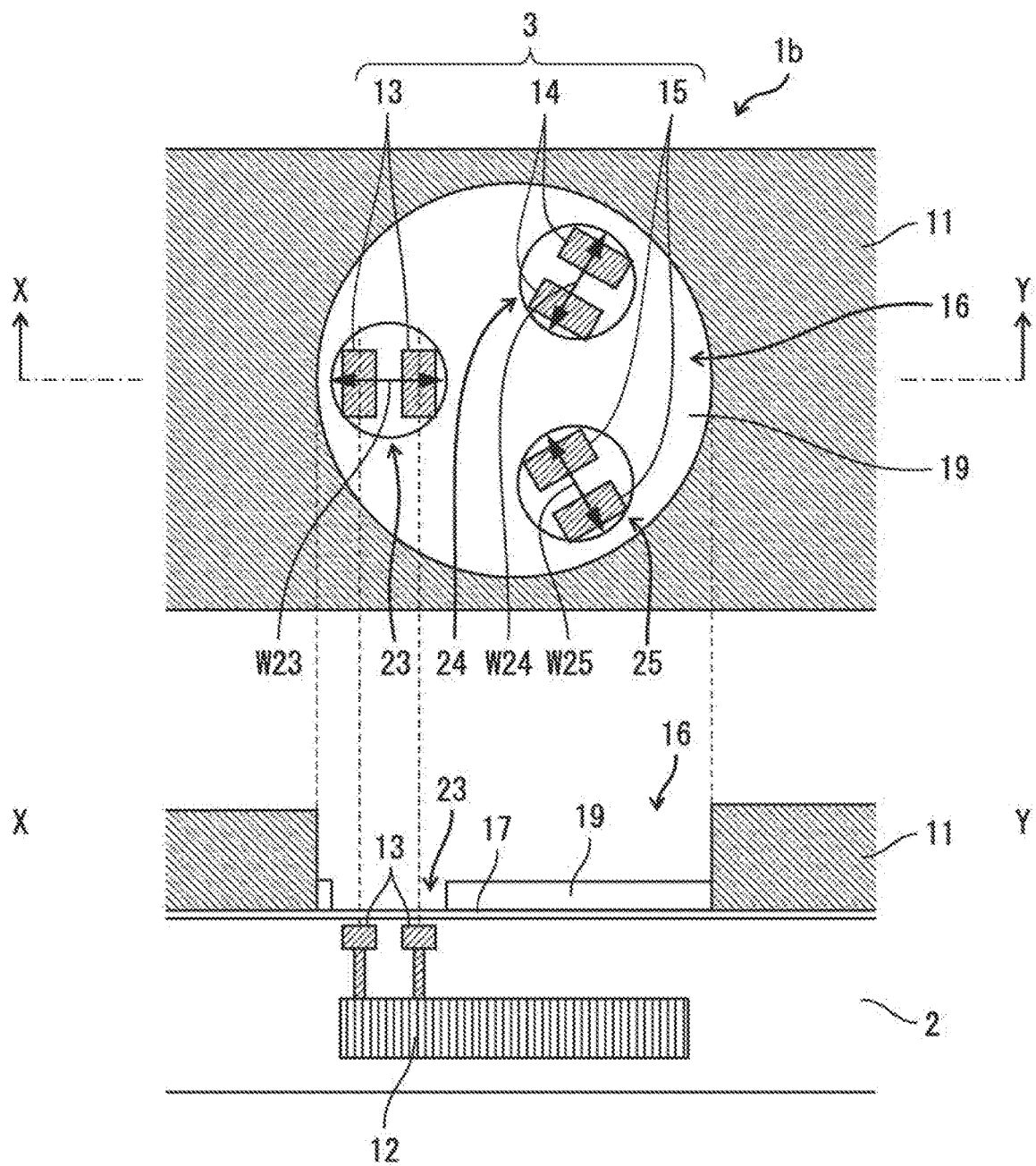
FIG. 5 is a plan view and a sectional view taken along a line X-Y each illustrating a configuration of an object trapping device according to Embodiment 2 of the invention.

FIG. 5 is a plan view and a sectional view taken along a line X-Y each illustrating a configuration of the object trapping device 1b according to Embodiment 2 of the invention. The object trapping device 1b includes a sub-well formation layer 19 in addition to the configuration of the object trapping device 1. The sub-well formation layer 19 is laminated on the protection film 17 in the well 16, in other words, laminated on the bottom surface of the well 16 and constituted by, for example, resin. The sub-well formation layer 19 is formed with three openings through which the protection film 17 is exposed and the three openings correspond to a first sub-well 23, a second sub-well 24, and a third sub-well 25. The first sub-well 23, the second sub-well 24, and the third sub-well 25 are respectively provided directly above the first electrode pair 13, directly above the second electrode pair 14, and directly above the third electrode pair 15. That is, each of the sub-wells is arranged above a corresponding one of the first electrode pair 13, the second electrode pair 14, and the third electrode pair 15.

A maximum width W23 of the first sub-well 23 is slightly wider than a maximum width of an object to be trapped by the first electrode pair 13. A maximum width W24 of the second sub-well 24 is slightly wider than a maximum width of an object to be trapped by the second electrode pair 14. A maximum width W25 of the third sub-well 25 is slightly wider than a maximum width of an object to be trapped by the third electrode pair 15.

In an outside of the first sub-well 23, a separation distance from the first electrode pair 13 is larger than that in an inside of the first sub-well 23 and the sub-well formation layer 19 is interposed, and therefore the first electrode pair 13 has a weak force of trapping an object. In an outside of the second sub-well 24, a separation distance from the second electrode pair 14 is larger than that in an inside of the second sub-well 24 and the sub-well formation layer 19 is interposed, and therefore the second electrode pair 14 has a weak force of trapping an object. In an outside of the third sub-well 25, a separation distance from the third electrode pair 15 is larger than that in an inside of the third sub-well 25 and the sub-well formation layer 19 is interposed, and therefore the third electrode pair 15 has a weak force of trapping an object.

That is, according to the object trapping device 1b, an area where the first electrode pair 13 has a strong force of trapping an object is able to be limited to the inside of the first sub-well 23. Moreover, according to the object trapping device 1b, an area where the second electrode pair 14 has a strong force of trapping an object is able to be limited to the inside of the second sub-well 24. Moreover, according to the object trapping device 1b, an area where the third electrode pair 15 has a strong force of trapping an object is able to be limited to the inside of the third sub-well 25. As a result, according to the object trapping device 1b, it is possible to reduce a possibility that each of the first electrode pair 13, the second electrode pair 14, and the third electrode pair 15 traps many objects without intention.

Figure 6:
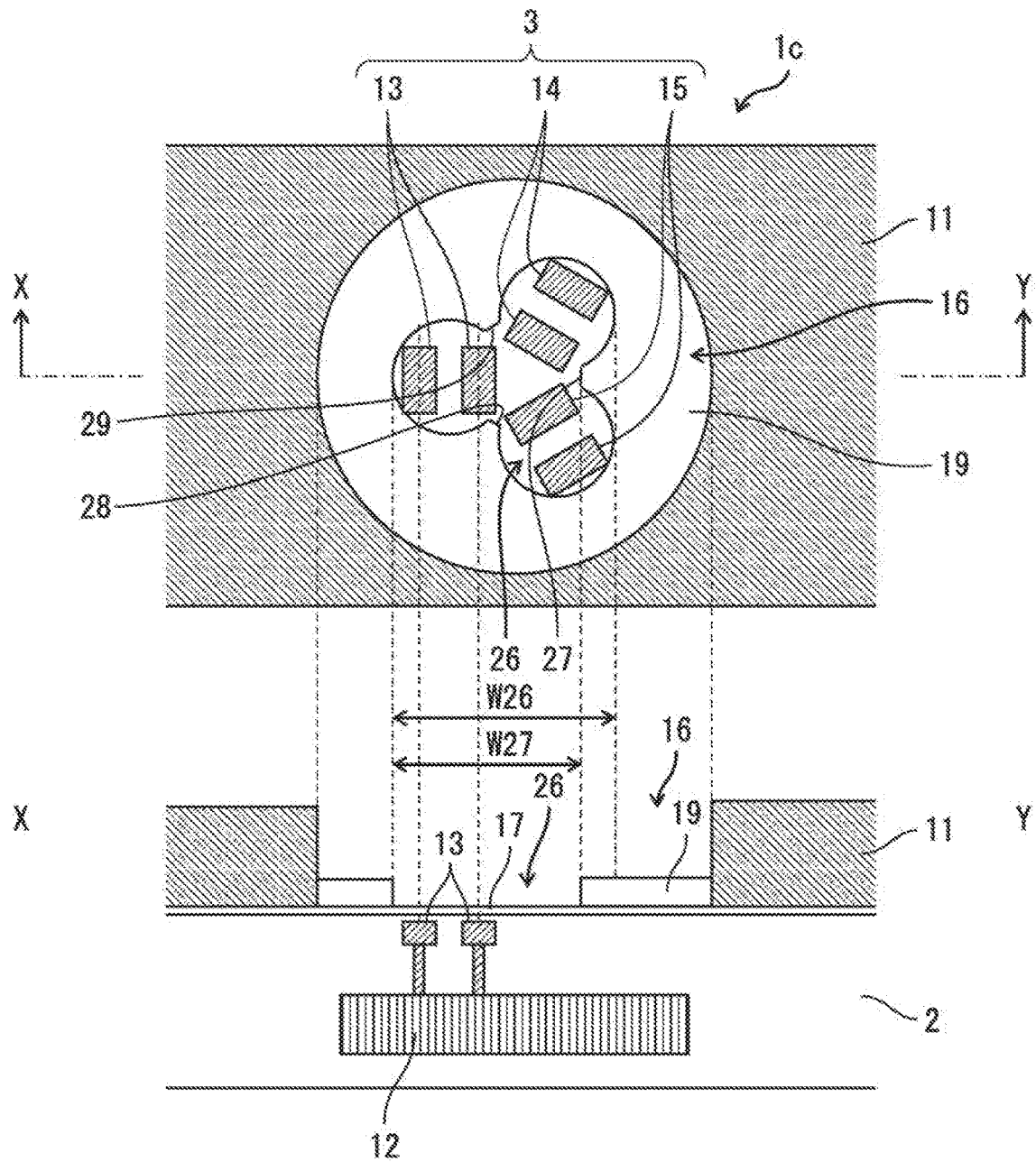
FIG. 6 is a plan view and a sectional view taken along a line X-Y each illustrating a configuration of a modified example of the object trapping device according to Embodiment 2 of the invention.

FIG. 6 is a plan view and a sectional view taken along a line X-Y each illustrating a configuration of the object trapping device 1c which is a modified example of the object trapping device 1b according to Embodiment 2 of the invention. In the object trapping device 1c, the first electrode pair 13, the second electrode pair 14, and the third electrode pair 15 are arranged so as to be closer to each other than those of the object trapping device 1b. Accordingly, the object trapping device 1c has a configuration in which the first sub-well 23, the second sub-well 24, and the third sub-well 25 in the object trapping device 1b are coupled to each other. In FIG. 6, a sub-well set 26 is obtained by forming the first sub-well 23, the second sub-well 24, and the third sub-well 25, which are coupled to each other, differently from those in the configuration of the object trapping device 1b.

Narrowed portions 27 to 29 are formed in the sub-well set 26. Each of the narrowed portions 27 to 29 is formed for the purpose of reducing a width of the sub-well set 26. For example, a width W27 of the sub-well set 26 when the narrowed portion 27 is formed is narrower than a width W26 of the sub-well set 26 when the narrowed portion 27 is not formed.

According to the object trapping device 1c, an area where each of the first electrode pair 13, the second electrode pair 14, and the third electrode pair 15 has a strong force of trapping an object is further limited. As a result, according to the object trapping device 1c, it is possible to further reduce the possibility that each of the first electrode pair 13, the second electrode pair 14, and the third electrode pair 15 traps many objects without intention.

Embodiment 3

Figure 7:
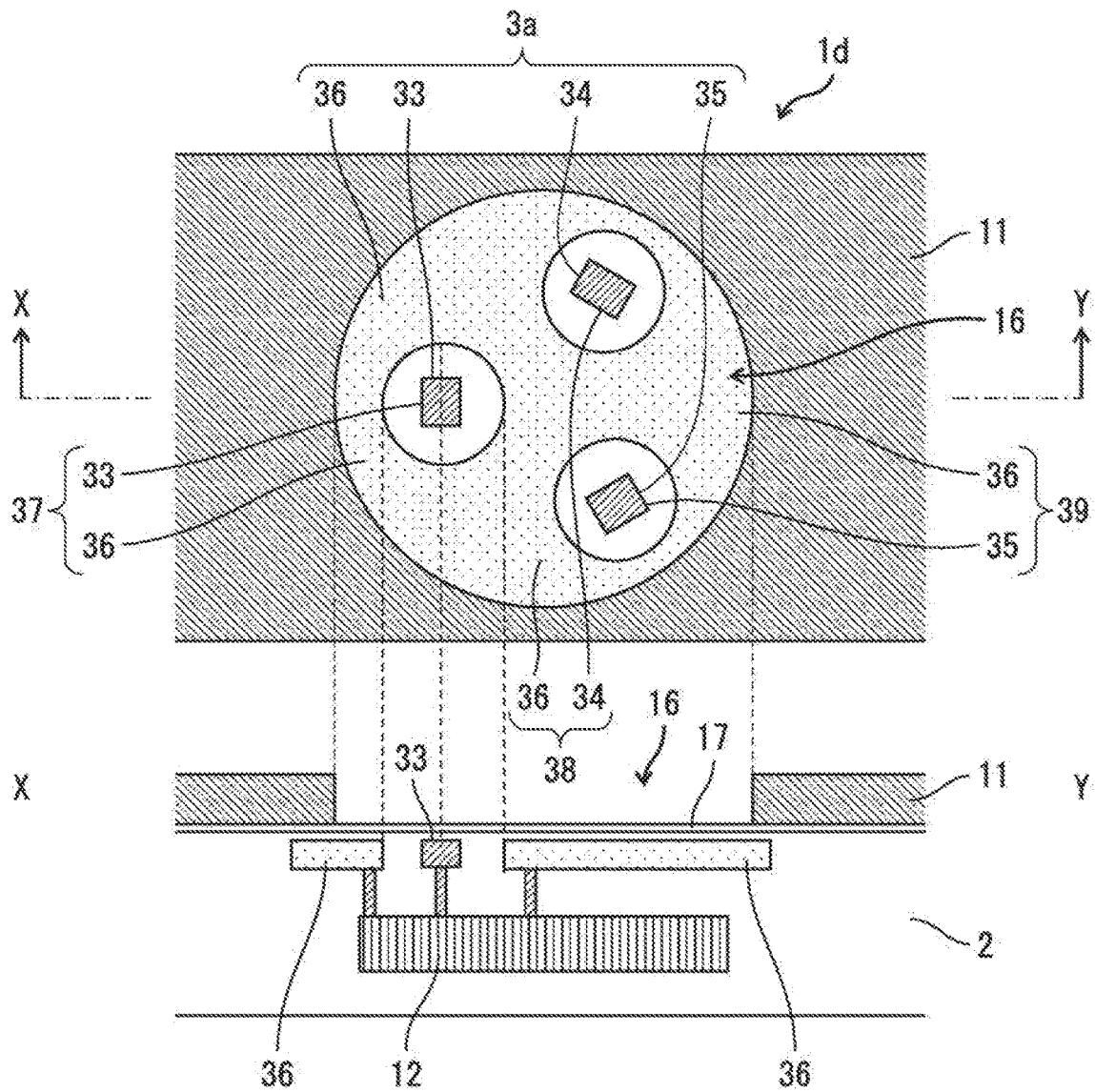
FIG. 7 is a plan view and a sectional view taken along a line X-Y each illustrating a configuration of an object trapping device according to Embodiment 3 of the invention.

FIG. 7 is a plan view and a sectional view taken along a line X-Y each illustrating a configuration of the object trapping device 1d according to Embodiment 3 of the invention. The object trapping device 1d is different from the object trapping device 1 in terms of including not the electrode pair group 3 but an electrode pair group 3a.

The electrode pair group 3a has a first electrode 33, a second electrode 34, a third electrode 35, and a common electrode 36. The first electrode 33, the second electrode 34, the third electrode 35, and the common electrode 36 are arranged in the bottom part of the well 16 in the semiconductor substrate 2 and connected to the control circuit 12. The first electrode 33 and the common electrode 36 are paired so as to form a first electrode pair 37 and the first electrode pair 37 has a function equivalent to that of the first electrode pair 13 of the object trapping device 1. The second electrode 34 and the common electrode 36 are paired so as to form a second electrode pair 38 and the second electrode pair 38 has a function equivalent to that of the second electrode pair 14 of the object trapping device 1. The third electrode 35 and the common electrode 36 are paired so as to form a third electrode pair 39 and the third electrode pair 39 has a function equivalent to that of the third electrode pair 15 of the object trapping device 1. In other words, an electrode of the first electrode pair 37 which is any of a plurality of electrode pairs and an electrode of the second electrode pair 38 which is any of the plurality of electrode pairs and different from the first electrode pair 37 are commonly used in a form of the common electrode 36. Similarly, an electrode of the second electrode pair 38 which is any of the plurality of electrode pairs and an electrode of the third electrode pair 39 which is any of the plurality of electrode pairs and different from the second electrode pair 38 are commonly used in a form of the common electrode 36. Similarly, an electrode of the third electrode pair 39 which is any of the plurality of electrode pairs and an electrode of the first electrode pair 37 which is any of the plurality of electrode pairs and different from the third electrode pair 39 are commonly used in a form of the common electrode 36. Note that, though the common electrode 36 is arranged in a whole of the bottom part of the well 16 other than a vicinity of the first electrode 33, a vicinity of the second electrode 34, and a vicinity of the third electrode 35 in the object trapping device 1d, the arrangement of the common electrode 36 in the bottom part of the well 16 is not particularly limited.

According to the object trapping device 1d, the electrodes constituting the electrode pair group 3a achieve a total area smaller than that of the electrode pair group 3 of the object trapping device 1. Thus, an effect that fluorescence from an object is less likely to be blocked by an electrode when the fluorescence is detected in the semiconductor substrate 2 is exerted.

Figure 8:
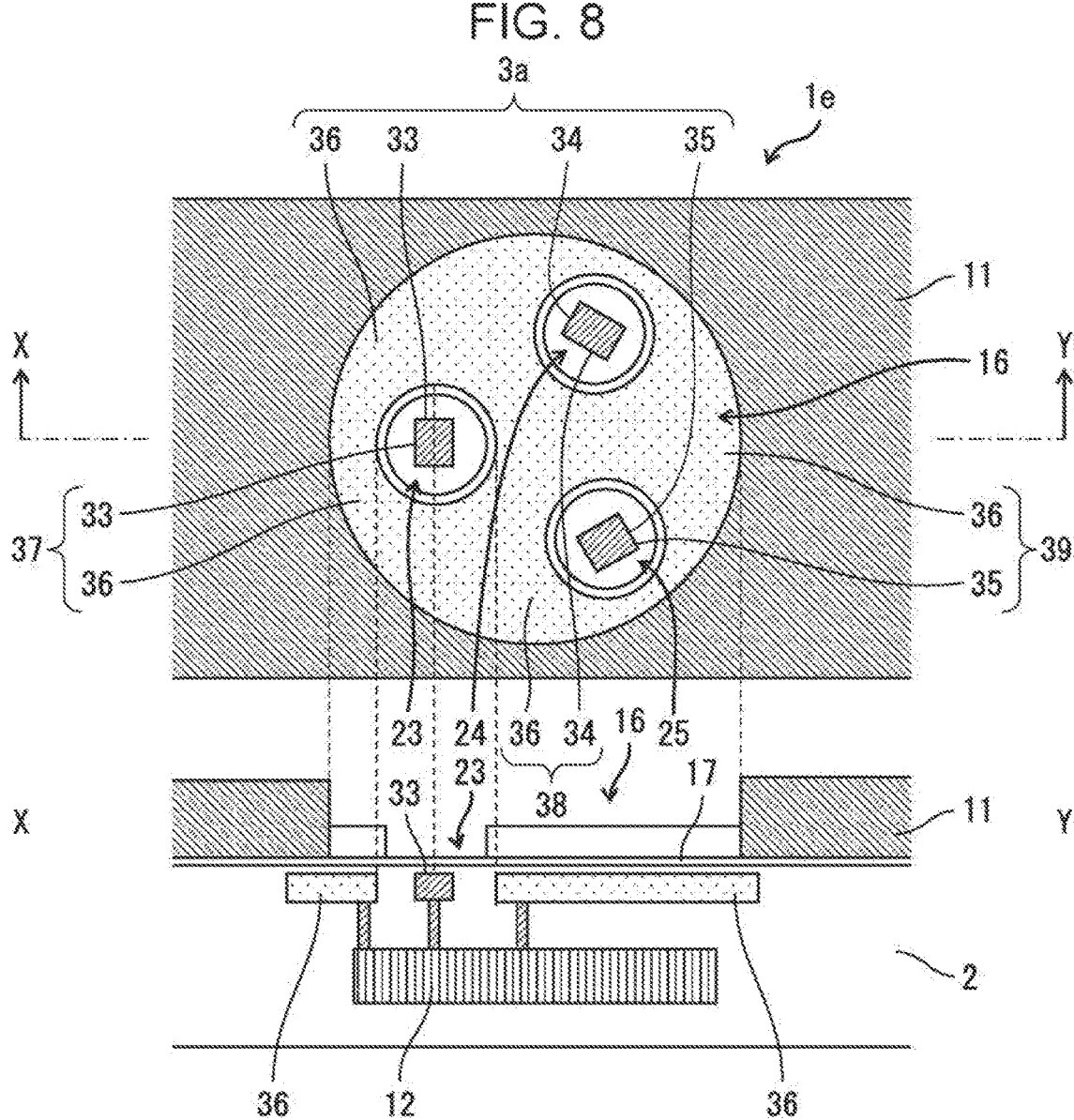
FIG. 8 is a plan view and a sectional view taken along a line X-Y each illustrating a configuration of a first modified example of the object trapping device according to Embodiment 3 of the invention.

FIG. 8 is a plan view and a sectional view taken along a line X-Y each illustrating a configuration of the object trapping device 1e which is a first modified example of the object trapping device 1d according to Embodiment 3 of the invention. The object trapping device 1e is different from the object trapping device 1b in terms of including not the electrode pair group 3 but the electrode pair group 3a. Note that, since not the electrode pair group 3 but the electrode pair group 3a is provided, the first sub-well 23, the second sub-well 24, and the third sub-well 25 are respectively formed directly above the first electrode 33, the second electrode 34, and the third electrode 35 in the object trapping device 1e. Accordingly, the object trapping device 1e is able to achieve both an effect by the object trapping device 1b and an effect by the object trapping device 1d.

Figure 9:
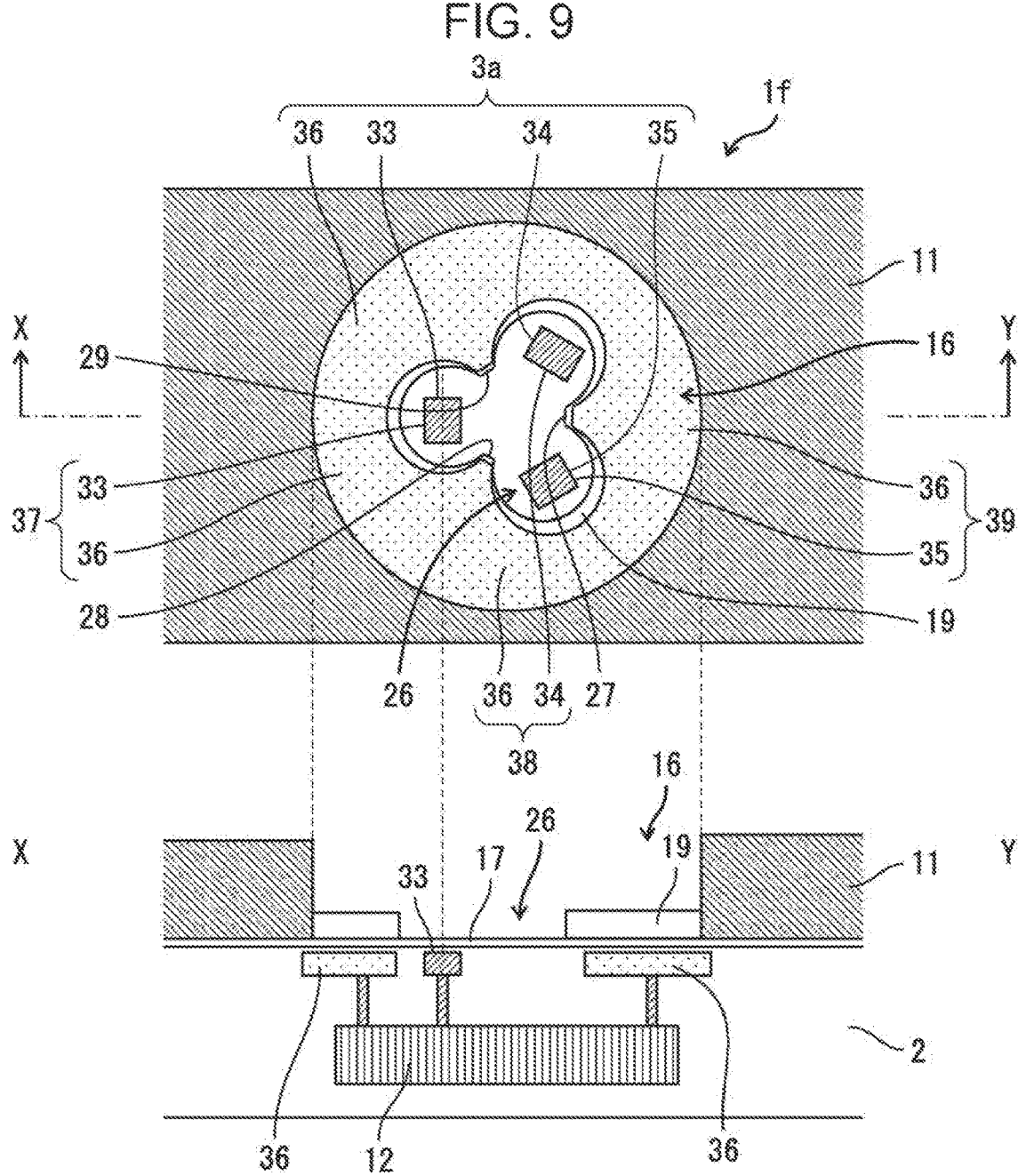
FIG. 9 is a plan view and a sectional view taken along a line X-Y each illustrating a configuration of a second modified example of the object trapping device according to Embodiment 3 of the invention.
Figure 11:
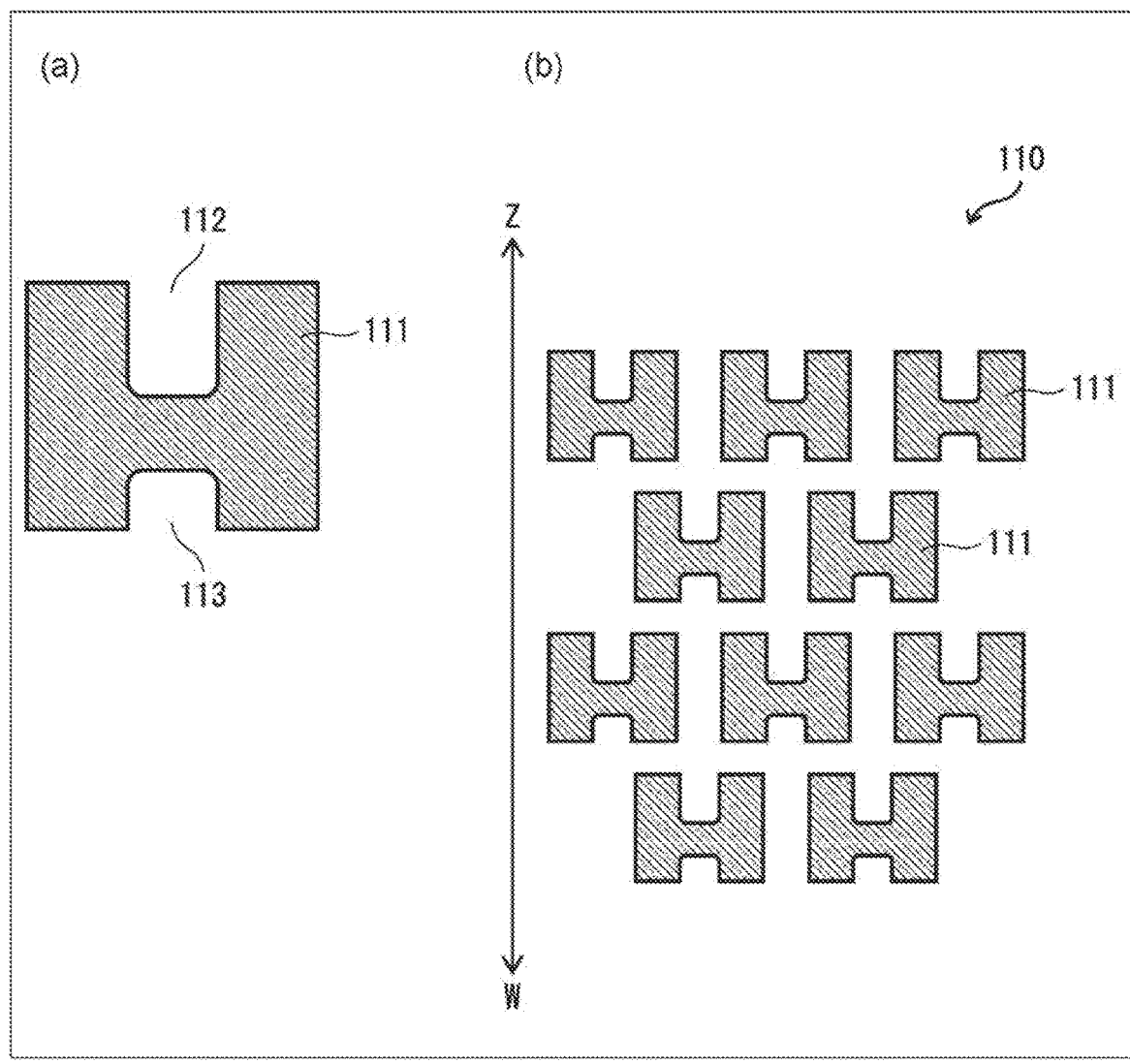
Figure 12:
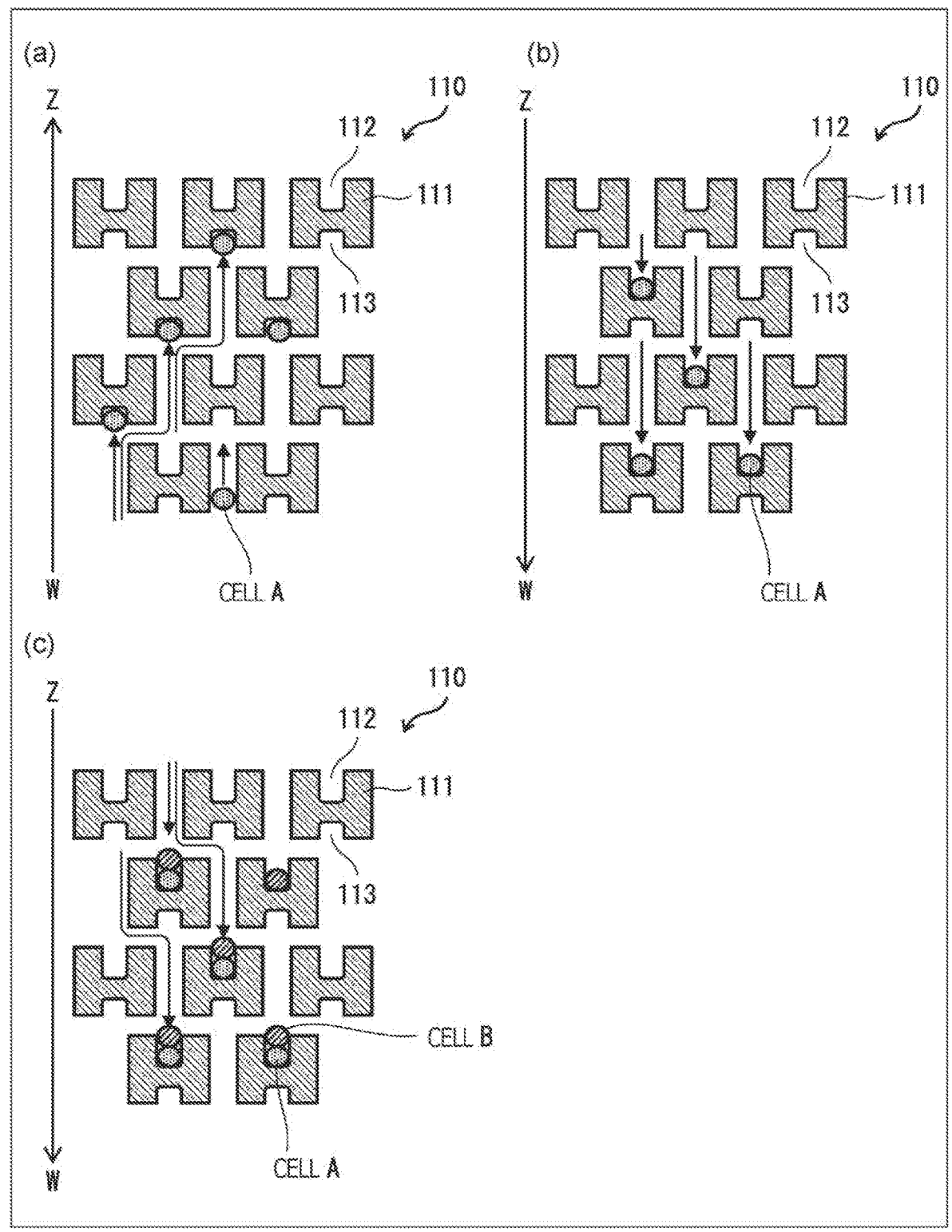

FIG. 9 is a plan view and a sectional view taken along a line X-Y each illustrating a configuration of the object trapping device 1f which is a second modified example of the object trapping device 1d according to Embodiment 3 of the invention. The object trapping device 1f is different from the object trapping device 1c in terms of including not the electrode pair group 3 but the electrode pair group 3a. Note that, since not the electrode pair group 3 but the electrode pair group 3a is provided, the sub-well set 26 is formed over a part directly above the first electrode 33, directly above the second electrode 34, and directly above the third electrode 35 in the object trapping device 1f. Accordingly, the object trapping device 1f is able to achieve both an effect by the object trapping device 1c and the effect by the object trapping device 1d.

FIG. 10 is a plan view and a sectional view taken along a line X-Y each illustrating a configuration of the object trapping device 1g which is a third modified example of the object trapping device 1d according to Embodiment 3 of the invention. The object trapping device 1g includes the photodiode 18 in addition to the configuration of the object trapping device 1f. Accordingly, the object trapping device 1g is able to achieve both an effect by the object trapping device 1a and an effect by the object trapping device 1f.

CONCLUSION

An object trapping device according to an aspect 1 of the invention includes a well, and an electrode pair group that is arranged in a bottom part of the well and includes a plurality of electrode pairs (the first electrode pair 13 to the third electrode pair 15), in which each of the plurality of electrode pairs in the electrode pair group is applied with an individual AC voltage and traps an object by dielectrophoresis generated in accordance with the AC voltage that is applied.

According to the aforementioned configuration, the plurality of electrode pairs attract and trap respective target objects by a principle of dielectrophoresis. Thus, according to the aforementioned configuration, it is possible to achieve trapping of a plurality of objects in a specific combination with high probability.

Further, according to the aforementioned configuration, by forming an object trapping device unit including a plurality of object trapping devices, it is possible to achieve different combinations of objects for the respective object trapping devices. Moreover, according to the aforementioned configuration, it is possible to easily seal the well by putting a lid on the well. Moreover, according to the aforementioned configuration, when there are three or more electrode pairs, three or more combinations of objects are able to be created by them.

Consequently, according to the aforementioned configuration, it is possible to efficiently trap a plurality of objects in a specific combination.

In the object trapping device according to an aspect 2 of the invention, each of sub-wells (the first sub-well 23 to the third sub-well 25) is arranged above a corresponding one of the plurality of electrode pairs in the aspect 1.

According to the aforementioned configuration, areas where the plurality of electrode pairs have a strong force of trapping an object are able to be limited to insides of the respective sub-wells arranged above the plurality of electrode pairs. As a result, according to the aforementioned configuration, it is possible to reduce a possibility that each of the plurality of electrode pairs traps many objects without intention.

In the object trapping device according to an aspect 3 of the invention, at least two of the sub-wells are coupled to each other and form a sub-well set in the aspect 2.

In the object trapping device according to an aspect 4 of the invention, a narrowed portion that reduces a width of the sub-well set is formed in the sub-well set in the aspect 3.

According to the aforementioned configuration, the respective areas where the plurality of electrode pairs have the strong force of trapping the object are further limited. As a result, according to the aforementioned configuration, it is possible to further reduce the possibility that each of the plurality of electrode pairs traps many objects without intention.

In the object trapping device according to an aspect 5 of the invention, an electrode of a first electrode pair that is any of the plurality of electrode pairs and an electrode of a second electrode pair that is any of the plurality of electrode pairs and different from the first electrode pair are commonly used in any of the aspects 1 to 4.

According to the aforementioned configuration, it is possible to reduce a total area of electrodes constituting the electrode pair group. Thus, an effect that fluorescence from an object is less likely to be blocked by an electrode when the fluorescence is detected in a semiconductor substrate is exerted.

The object trapping device according to an aspect 6 of the invention further includes a photodiode arranged below the electrode pair group in any of the aspects 1 to 5.

According to the aforementioned configuration, the object trapping device is suitable for an experiment to evaluate an interaction between a plurality of cells by generation of a fluorescent material. That is, excitation light is radiated by a laser diode or the like to the well from above the well, the fluorescent material is excited by the excitation light, and light caused by the excitation is received by the photodiode. Then, by using the light received by the photodiode for evaluation of an interaction between a plurality of cells, the evaluation is able to be conducted without using a fluorescence microscope.

In the object trapping device according to an aspect 7 of the invention, at least one of the plurality of electrode pairs is able to generate an electric field to disrupt a cell membrane in any of the aspects 1 to 6.

The object trapping device according to an aspect 8 of the invention further includes a cell disrupting electrode that generates an electric field to disrupt a cell membrane in any of the aspects 1 to 6.

According to the configurations of the aspects 7 and 8, when an object trapped by the object trapping device is a cell, an inside gene is able to be analyzed by disrupting a membrane of the cell.

An object trapping device unit according to an aspect 9 of the invention includes a first object trapping device that is the aforementioned object trapping device, and a second object trapping device that is the aforementioned object trapping device and is different from the first object trapping device, in which the second object trapping device traps a substance, which is not trapped by the first object trapping device, as the object.

According to the aforementioned configuration, it is possible to achieve different combinations of objects for the respective object trapping devices.

The invention is not limited to each of the embodiments described above, and may be modified in various manners within the scope indicated in the claims and an embodiment achieved by appropriately combining technical means disclosed in each of different embodiments is also encompassed in the technical scope of the invention.

Further, by combining the technical means disclosed in each of the embodiments, a new technical feature may be formed.

REFERENCE SIGNS LIST 1, 1a to 1g object trapping device
1U object trapping device unit
1_1 first object trapping device
1_2 second object trapping device
2 semiconductor substrate
3, 3', 3a electrode pair group
11 well formation layer
12, 12', 12a control circuit
13, 13', 13_1, 13_2, 37 first electrode pair
14, 14', 14_1, 14_2, 38 second electrode pair
15, 15', 15_1, 152, 39 third electrode pair
16, 16' well
17 protection film
18 photodiode
19 sub-well formation layer
23 first sub-well (sub-well)
24 second sub-well (sub-well)
25 third sub-sell (sub-well)
26 sub-well set
27 to 29 narrowed portion
33 first electrode
34 second electrode
35 third electrode
36 common electrode
131, 141, 151 switch
132, 142, 152 switch setting unit
133, 143, 153 memory
134, 144, 154 control unit
161, 162, 171, 172, 181, 182 voltage source
C, D, E, F_1, F_2, G_1, G_2, H_1, H_2 cell (object)

The invention claimed is:

1. An object trapping device comprising:
a well;
an electrode pair group that is arranged below the well and includes a plurality of electrode pairs;
a sub-well set arranged inside the well and above the electrode pair group,
the sub-well set including a plurality of sub-wells,
the plurality of sub-wells each being arranged above a corresponding one of the plurality of electrode pairs,
the plurality of sub-wells each having a circular shape,
on the top view of the object trapping device, the sub-well set having a trefoil shape formed-by merging respective side surfaces of the plurality of sub-wells,
each of the plurality of electrode pairs in the electrode pair group being applied with an individual AC voltage and trapping an object by dielectrophoresis generated in accordance with the AC voltage that is applied.

2. The object trapping device according to claim 1, wherein an electrode of a first electrode pair that is any of the plurality of electrode pairs and an electrode of a second electrode pair that is any of the plurality of electrode pairs and different from the first electrode pair are commonly used in a form of a common electrode.

3. The object trapping device according to claim 1 further comprising a photodiode arranged below the electrode pair group.

4. The object trapping device according to claim 1, wherein at least one of the plurality of electrode pairs is able to generate an electric field to disrupt a cell membrane.

5. The object trapping device according to claim 1 further comprising a cell disrupting electrode that generates an electric field to disrupt a cell membrane.

* * * * *